(12) United States Patent
Rui et al.

(10) Patent No.: US 10,631,815 B2
(45) Date of Patent: Apr. 28, 2020

(54) SCATTER CORRECTION TECHNIQUE FOR USE WITH A RADIATION DETECTOR

(71) Applicant: General Electric Company, Schenectady, NY (US)

(72) Inventors: Xue Rui, Clifton Park, NY (US); Yannan Jin, Schenectady, NY (US); Biju Jacob, Schenectady, NY (US); Brian David Yanoff, Schenectady, NY (US); Uwe Wiedmann, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 519 days.

(21) Appl. No.: 15/591,926

(22) Filed: May 10, 2017

(65) Prior Publication Data

US 2018/0328863 A1    Nov. 15, 2018

(51) Int. Cl.
| | |
|---|---|
| A61B 6/00 | (2006.01) |
| G01N 23/046 | (2018.01) |
| A61B 6/03 | (2006.01) |
| G01T 1/24 | (2006.01) |

(52) U.S. Cl.
CPC ........... *A61B 6/5282* (2013.01); *A61B 6/032* (2013.01); *A61B 6/4291* (2013.01); *G01N 23/046* (2013.01); *G01T 1/242* (2013.01)

(58) Field of Classification Search
CPC ..... A61B 6/032; A61B 6/4233; A61B 6/4241; A61B 6/4266; A61B 6/4291; A61B 6/5282
See application file for complete search history.

(56) References Cited

U.S. PATENT DOCUMENTS

| | | | |
|---|---|---|---|
| 6,618,466 | B1 | 9/2003 | Ning |
| 6,639,964 | B2 | 10/2003 | Schneider et al. |
| 7,463,712 | B2 | 12/2008 | Zhu et al. |
| 8,238,521 | B2 | 8/2012 | McKim et al. |
| 8,705,827 | B2 | 4/2014 | Zhu et al. |
| 9,087,619 | B2 | 7/2015 | Hsieh et al. |
| 2017/0265833 | A1* | 9/2017 | Danielsson .......... A61B 6/4233 |

OTHER PUBLICATIONS

Hademenos, George J., et al.; "Influence of Phantom Size, Shape, and Density, and Collimator Selection on the Dual Photopeak Window Scatter Correction Method [SPECT]", IEEE Transactions on Nuclear Science, vol. 41, Issue 1, pp. 364-368, Feb. 1994.
Siewerdsen, J.H., et al.; "A Simple, Direct Method for X-ray Scatter Estimation and Correction in Digital Radiography and Cone-Beam CT", Medical Physics, vol. 33, pp. 187-197, Jan. 2006.
Kangasmaa, Tuija, et al.; "Optimisation of Simultaneous TI-201/Tc-99m Dual Isotope Reconstruction with Monte-Carlo-Based Scatter Correction", International Journal of Molecular Imaging, http://www.hindawi.com/journals/ijmi/2012/695632/, Oct. 2012.
Asi, Mahsa Norri, et al.; "Evaluation of Six Scatter Correction Methods Based on Spectral Analysis in 99mTc SPECT Imaging using SIMIND Monte Carlo Simulation", U.S. National Library of Medicine, pp. 189-197, Oct.-Dec. 2013.

* cited by examiner

*Primary Examiner* — Chih-Cheng Kao (57) ABSTRACT

The present approach relates to scatter correction of signals acquired using radiation detectors on a pixel-by-pixel basis. In certain implementations, the systems and methods disclosed herein facilitate scatter correction for signals generated using a detector having segmented detector elements, such as may be present in an energy-resolving, photon-counting CT imaging system.

20 Claims, 9 Drawing Sheets

SCATTER CORRECTION TECHNIQUE FOR USE WITH A RADIATION DETECTOR

BACKGROUND

Embodiments of the present specification relate generally to radiation detectors, and more particularly to scatter technique approaches for use with radiation detectors.

In an imaging system, such as a computed tomography (CT) imaging system, a fan shaped X-ray beam is emitted towards an object such as a patient or a piece of luggage to image a region of interest in the object. The beam is typically attenuated by the object. Subsequently, the attenuated beam is incident on a CT detector having an array of detector elements. In response to the attenuated beam, the detector elements of the array generate respective electrical signals representative of internal information of the object. These electrical signals are processed by a data processing unit to generate an image representative of the region of interest in the object.

Reconstruction of images from the acquired data is generally based upon the assumption that X-ray photons have traveled in a straight path from the X-ray emission focal spot to the detector element at which the respective photon is detected. However, some number of X-ray photons may be deflected or otherwise travel in a non-linear path (i.e., scattered) before reaching the detector elements on which they generate a signal. Such scattered photons generate an aberrant indication of attenuation at the detector element that may manifest as noise or other image irregularities (i.e., artifacts) in the reconstructed image. Thus, it may be of interest to find approaches for addressing scatter-related signal in an X-ray image acquisition.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one implementation, a method is provided for reducing scatter signal in a computed tomography (CT) system comprising an X-ray source and a pixelated detector. In accordance with aspects of this implementation, for each respective segment of a detector element comprising a plurality of segments, a respective response signal is acquired. For the detector element, a primary signal substantially free of scatter signal is estimated based on readout signals from one or more of the segments of the detector element. Based upon the estimated primary signal, a scatter signal at one or more segments of the detector element is estimated and corrected for at the one or more segments to generate scatter-corrected readout signals.

In a further implementation, a computed tomography (CT) imaging system is provided. In accordance with aspects of this implementation, the CT imaging system includes a radiation source configured to emit radiation and a pixelated detector configured to generate signals in response to the emitted radiation. The pixelated detector comprises a plurality of detector elements, each detector element comprising a plurality of segments offset in the direction of radiation propagation. At least a portion of the detector elements are separated by radiation blocking plates in at least one dimension. The CT imaging system further includes a processing component configured to receive signals read out from the pixelated detector, wherein a signal is read out for each segment of each detector element. For each detector element the processing component: estimates a primary signal substantially free of scatter signal based on readout signals from one or more of the segments of the detector element; based upon the estimated primary signal, estimates a scatter signal at one or more segment of the detector element; corrects for the estimated scatter signal at the one or more segments to generate scatter-corrected readout signals for the detector element; and for the combined scatter corrected readout signals from each detector element, reconstructs an image using the scatter corrected readout signals.

In an additional implementation, one or more non-transitory computer-readable media storing processor-executable instructions are provided. In accordance with aspects of this implementation, the instructions, when executed by one or more processors, cause the one or more processors to perform acts comprising: for each respective segment of a detector element comprising a plurality of segments, acquiring a respective response signal; for the detector element, estimating a primary signal substantially free of scatter signal based on readout signals from one or more of the segments of the detector element; and based upon the estimated primary signal, estimating a scatter signal at one or more segment of the detector element and correcting for the estimated scatter signal at the one or more segments to generate scatter-corrected readout signals.

DRAWINGS

These and other features and aspects of embodiments of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion may be provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as tomographic image reconstruction for industrial Computed Tomography (CT) used in non-destructive inspection of manufactured parts or goods (i.e., quality control or quality review applications), and/or the non-invasive inspection of packages, boxes, luggage, and so forth (i.e., security or screening applications). In general, the present approaches may be useful in any imaging or screening context or image processing field where a set or type of acquired data undergoes a reconstruction process to generate an image or volume.

Embodiments of the present disclosure relate to scatter correction algorithms for use with a signal generated by a radiation detectors. In particular, the systems and methods disclosed herein facilitate scatter correction for signals generated using a detector having vertically-segmented detector element, such as may be present in energy-resolving, photon-counting CT imaging system.

As discussed herein, in certain implementations, the radiation detector is an energy-resolving, photon-counting CT imaging system that includes a detector having vertically-segmented detector elements (i.e., pixels) from which signals are readout from the respective segments at different depths. The vertically-segmented detector elements typically employ shielding that separates the detector elements from one another in at least one dimension, effectively providing some degree of scatter absorption along the length of the detector element. As a result, the scatter-to-primary (SPR) ratio (defined as $$\left( \frac{\text{scatter signal}}{\text{primary signal}} \right)$$

observed at different segments within the detector element varies based on depth, with higher segments (i.e., those closer to the X-ray source) experience more scatter (i.e., have a higher SPR) than those segments that are lower, i.e., further from the X-ray source. The present approach leverages this difference in SPR at different depths within the detector element to correct for scatter within different segments of each detector element.

Figure 1:
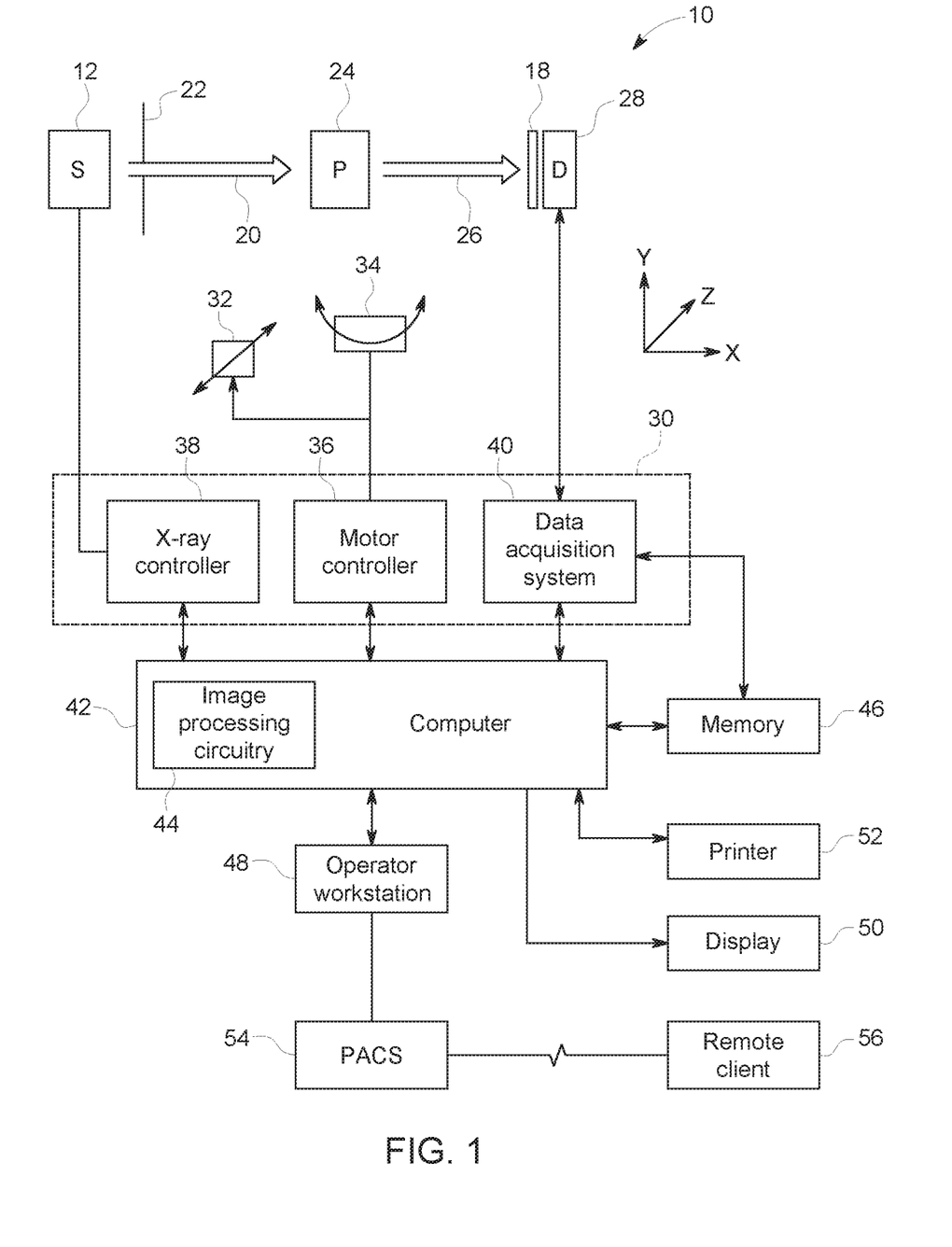
FIG. 1 is a block diagram representation of a computed tomography (CT) system, in accordance with aspects of the present disclosure.

With this in mind, as used herein, the terms "pixel", and "segmented detector" are used equivalently to denote detector elements of a pixelated detector. As used herein, the term "gain factor" refers to a gain value that is applied to a response signal of a segmented detector. Further, as used herein, the term "scattering signal" refers to a component of a detector signal representative of X-ray photons that have undergone a directional change in their flight between the X-ray source and detector. Furthermore, the term "pile-up" refers to a detector response exhibiting a saturating response when the density of X-ray photons increases beyond a threshold value. As used here, the term "channel" is used equivalently and interchangeably to refer to a combination of a plurality of segments and corresponding read-out electronics of a detector, where the combination is configured to generate a response signal. The term "response" refers to a response signal obtained from a segmented detector. In the case of the segmented detector, the response signal includes a plurality of photon counts corresponding to a plurality of energy bins, e.g., different discrete energy ranges corresponding to the energy of a respective X-ray photon. Each of the photon count values among the plurality of photon counts is generated by a photon counter associated with a segment of the segmented detector With the preceding discussion in mind, FIG. 1 illustrates an embodiment of an imaging system 10 for acquiring and processing image data using segmented detector elements and anti-scatter correction in accordance with structures and approaches discussed herein. In the illustrated embodiment, system 10 is a computed tomography (CT) system designed to acquire X-ray projection data and to reconstruct the projection data into volumetric reconstructions for display and analysis. The CT imaging system 10 includes one or more X-ray sources 12, such as one or more X-ray tubes or solid state emission structures which allow X-ray generation at one or more energy spectra during an imaging session.

In certain implementations, the source 12 may be positioned proximate to a pre-patient collimator 22 that may be used to steer the X-ray beam 20, to define the shape (such as by limiting off-angle emissions) and/or extent of a high-intensity region of the X-ray beam 20, to control or define the energy profile of the X-ray beam 20, and/or to otherwise limit X-ray exposure on those portions of the patient 24 not within a region of interest. In practice, the filter assembly or beam shaper 22 may be incorporated within the gantry, between the source 12 and the imaged volume.

The X-ray beam 20 passes into a region in which the subject (e.g., a patient 24) or object of interest (e.g., manufactured component, baggage, package, and so forth) is positioned. The subject attenuates at least a portion of the X-ray photons 20, resulting in attenuated X-ray photons 26 that impinge upon a pixelated detector array 28 formed by a plurality of segmented detector elements (e.g., pixels) arranged in an m×n array. The detector 28 may be an energy-integrating detector, a photon-counting detector, an energy-discriminating detector, or any other suitable radiation detector. By way of example, the detector 28 may be an energy-discriminating photon-counting detector, whose output signals, generated in response to X-rays incident on the detector, convey information about the number and energy of photons that impact the detector at measured positions and over a time interval corresponding to a scan or imaging session. For example, the output signals of the elements of the detector 28 may constitute photon counts for each of a plurality of energy bins (i.e., energy ranges) for a given acquisition interval. The electrical signals are acquired and processed to generate one or more projection datasets. In the depicted example, the detector 28 is coupled to the system controller 30, which commands acquisition of the digital signals generated by the detector 28.

A system controller 30 commands operation of the imaging system 10 to execute filtration, examination and/or calibration protocols, and may process the acquired data. With respect to the X-ray source 12, the system controller 30 furnishes power, focal spot location, control signals and so forth, for the X-ray examination sequences. In accordance with certain embodiments, the system controller 30 may control operation of the filter assembly 22, the CT gantry (or other structural support to which the X-ray source 12 and detector 28 are attached), and/or the translation and/or inclination of the patient support over the course of an examination.

In addition, the system controller 30, via a motor controller 36, may control operation of a linear positioning subsystem 32 and/or a rotational subsystem 34 used to move the subject 24 and/or components of the imaging system 10, respectively. For example, in a CT system, the radiation source 12 and detector 28 rotate about the object (e.g., patient 24) to acquire X-ray transmission data over a range of angular views. Thus, in a real-world implementation, the imaging system 10 is configured to generate X-ray transmission data corresponding to each of the plurality of angular positions (e.g., 360°, 180°+a fan beam angle ($\alpha$), and so forth) covering an entire scanning area of interest.

The system controller 30 may include signal processing circuitry and associated memory circuitry. In such embodiments, the memory circuitry may store programs, routines, and/or encoded algorithms executed by the system controller 30 to operate the imaging system 10, including the X-ray source 12 and/or filter assembly 22, and to process the digital measurements acquired by the detector 28 in accordance with the steps and processes discussed herein. In one embodiment, the system controller 30 may be implemented as all or part of a processor-based system.

The source 12 may be controlled by an X-ray controller 38 contained within the system controller 30. The X-ray controller 38 may be configured to provide power, timing signals, and/or focal spot size and spot locations to the source 12. In addition, in some embodiments the X-ray controller 38 may be configured to selectively activate the source 12 such that tubes or emitters at different locations within the system 10 may be operated in synchrony with one another or independent of one another or to switch the source between different energy profiles during an imaging session.

The system controller 30 may include a data acquisition system (DAS) 40. The DAS 40 receives data collected by readout electronics of the detector 28, such as digital signals from the detector 28. The DAS 40 may then convert and/or process the data for subsequent processing by a processor-based system, such as a computer 42. In certain implementations discussed herein, circuitry within the detector 28 may convert analog signals of the detector to digital signals prior to transmission to the data acquisition system 40. The computer 42 may include or communicate with one or more non-transitory memory devices 46 that can store data processed by the computer 42, data to be processed by the computer 42, or instructions to be executed by image processing circuitry 44 of the computer 42. For example, a processor of the computer 42 may execute one or more sets of instructions stored on the memory 46, which may be a memory of the computer 42, a memory of the processor, firmware, or a similar instantiation. By way of example, the image processing circuitry 44 of the computer 42 may be configured to generate a diagnostic image. In one embodiment, the diagnostic image is a real-time image obtained using image reconstruction techniques applied to the plurality of scatter-corrected signals obtained from the plurality of pixels 102. In one embodiment, the diagnostic image is a scatter-corrected CT image displayed on a display device 50 for assisting a medical practitioner.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data (e.g., soft tissue images, bone images, segmented vascular trees, and so on), material basis images, and/or material decomposition results, and so forth. Additionally, the system 10 may include a printer 52 coupled to the operator workstation 48 and configured to print any desired measurement results. The display 50 and the printer 52 may also be connected to the computer 42 directly (as shown in FIG. 1) or via the operator workstation 48. Further, the operator workstation 48 may include or be coupled to a picture archiving and communications system (PACS) 54. PACS 54 may be coupled to a remote system or client 56, radiology department information system (RIS), hospital information system (HIS) or to an internal or external network, so that others at different locations can gain access to the image data.

Figure 2:
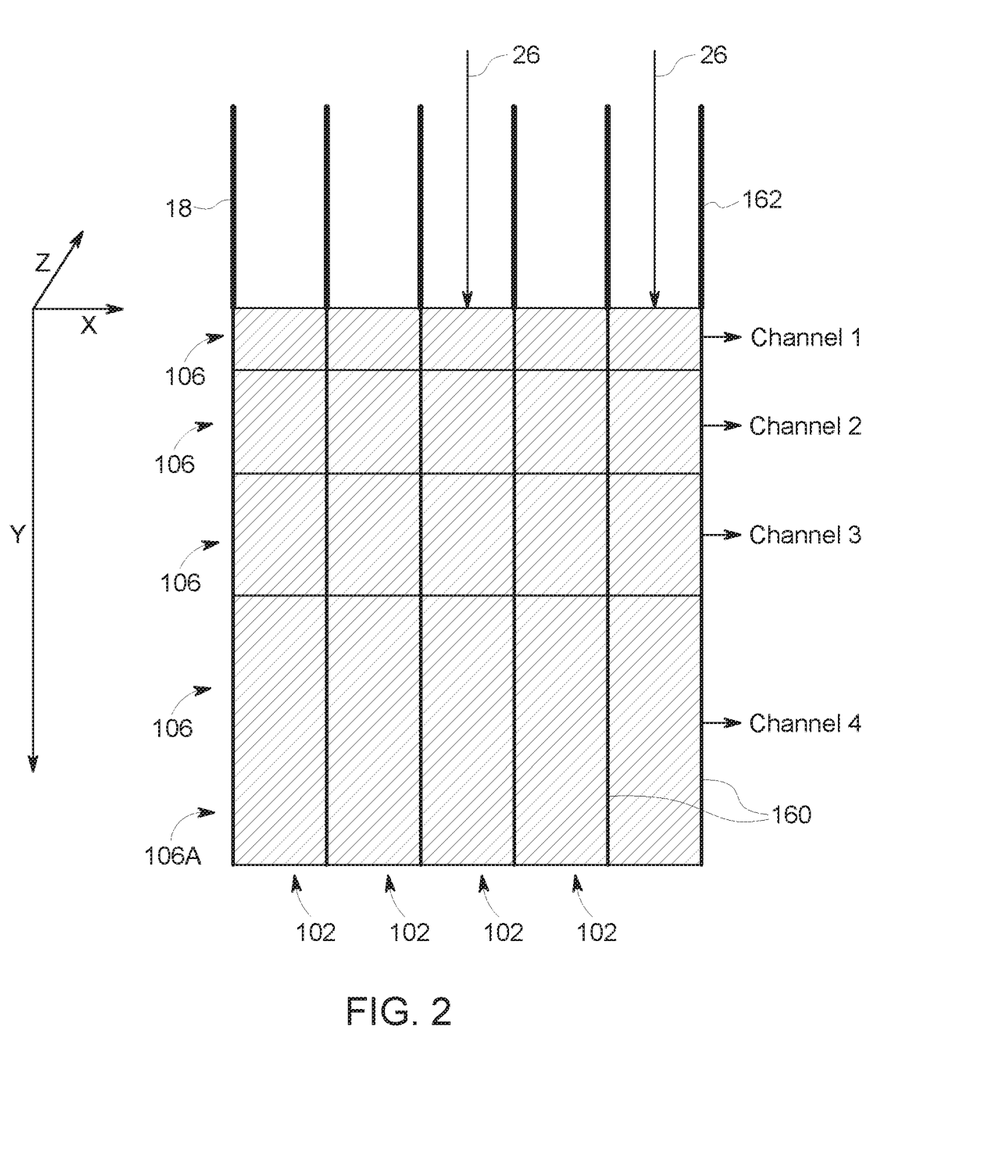
FIG. 2 depicts a side-sectional view of a segmented pixelated detector, in accordance with aspects of the present disclosure.

With the preceding discussion of an overall imaging system 10 in mind, and turning to FIG. 2, a detector 28 for use in accordance with the present approach is shown in greater detail. In particular, in one embodiment the detector 28 may be a direct-conversion type detector (i.e., a detector that does not employ a scintillator intermediary), such as a detector based on semiconductor materials as the active material, such as cadmium telluride/cadmium zinc telluride (CdTe/CZT) or silicon, that generate a measurable signal when the semiconductor sensor is itself exposed to X-ray photons. In certain implementations discussed herein, a detector 28 employing segmented silicon strips as the detector elements (i.e., pixels) is described.

By way of example, and turning briefly to FIG. 2, each of the plurality of pixels 102 includes a detector element (such as a silicon strip) having a plurality of segments 106 (e.g., 4, 5, 6, 7, 8, or 9 segments) disposed at a plurality of depths with respect to the path of the emitted X-rays 26 with respect to the surface of the pixels 102 facing the source 12. It may be noted that, for the purpose of simplicity the depicted silicon strips are depicted as being contiguous. However, in practice, the silicon strips may be formed using two or more silicon wafers so as to allow a space between the two wafers to facilitate cooling and placement of electrical circuitry. Such discontinuities though, if present for practical manufacturing or fabrication concerns, do not impact the concepts presently presented.

As used herein, the direction traveled by the X-rays 26 (i.e., the direction of X-ray propagation) with respect to the source-facing surface of the pixels 102 may be denoted as "vertical" (corresponding to the Y-dimension in FIG. 2) and/or may construed as corresponding to a depth dimension so as to provide a geometric frame of reference, hence such a segmented detector element may be described as vertically segmented. As will be appreciated, however, such geometric characterization does not necessarily denote absolute position or orientation information, but is merely intended to simply discussion by providing a consistent contextual framework.

As may be appreciated, in the context of a pixelated detector 28 for use in CT, the detector 28 includes a plurality of such pixels 102 in two dimensions for each angular position among the multiple angular positions at which X-rays are incident on the detector 28. The plurality of vertical segments 106 within a pixel 102 may have different heights and/or thicknesses and generate response signals that may be used for reducing effect of artifacts in signals generated by the pixels 102 of the pixelated detector 28. Further, as shown in FIG. 2, the pixels 102 are separated laterally by anti-scatter plates 160 formed of an X-ray blocking material (e.g., a 20 μm sheath of tungsten) along the X-axis. The plates 160 help to prevent internal scatter within the detector, as discussed herein and effectively act to collimate the X-rays traveling through the detector pixels 102 such that segments 106 closer to the surface facing the X-ray source are more likely to experience scatter events than those further from the surface. Additionally, in the depicted example, an anti-scatter grid or collimator 18 is positioned proximate to the surface of the detector 28. As may be appreciated, both the anti-scatter grid 18 and plates 160 may be made of a material or materials that absorbs or otherwise block X-ray photons. Thus, X-ray photons striking the septa of the anti-scatter collimator 18 or the plates 160, after being reflected or deflected by the object 24, or otherwise moving at an angle relative to the septa of the anti-scatter collimator 18 or plates 160, are stopped in their path. Conversely, X-ray photons traveling in a relatively straight path from the X-ray source 12 to the detector 28 are unimpeded by the anti-scatter collimator 18 and plates 160. It may be noted that, due to the presence of the plates 160 within the body of the detector 28 which serve to collimate the X-rays 26, in other implementations, the anti-scatter grid 18 having septa 162 may be excluded or, alternatively, may be significantly smaller than a conventional anti-scatter grid due to the collimation provided by the internal plates 160. In one such embodiment where a separate anti-scatter grid 18 is omitted, the plates 160 may extend (for example 5 mm to 10 mm) above the surface of the uppermost segments 106 to remove the scatter signal.

While the present example, depicts the pixels 102 as being laterally separated by plates 160 in the X-dimension, the pixels 102 may, in one implementation, be separated along the Z-dimension by electrical bias. By way of example, an implementation of a pixel 102 may measure ~0.4 to 0.5 mm in the X-dimension and 0.5 mm in the Z-dimension and have an absorption length of between about 20 mm to about 80 mm (e.g., 30 mm or 60 mm) in the Y-dimension, though other configurations are possible and fall within the scope of the present disclosure.

In the depicted example, the detector elements in the form of pixels 102 are segmented such that the segments 106 at different depths are of different thicknesses. For example, in the depicted example the segments 106 increase in thickness as their depth in the Y-direction increases. Thickness of segments 106 in the Y-dimension may be based on obtaining uniform count rates along the length of the pixel 102.

In accordance with present approaches, the segments 106 at different depths each correspond to a different readout channel. Thus, in this example, there are four segments 106 (i.e., readout channels) for any given pixel 102. As discussed in greater detail below, each segment 106 of each pixel 102 may be read out by a given readout channel into a plurality of energy ranges (i.e., energy bins) to generate a photon count for each energy bin for a given readout interval or period.

Figure 3:
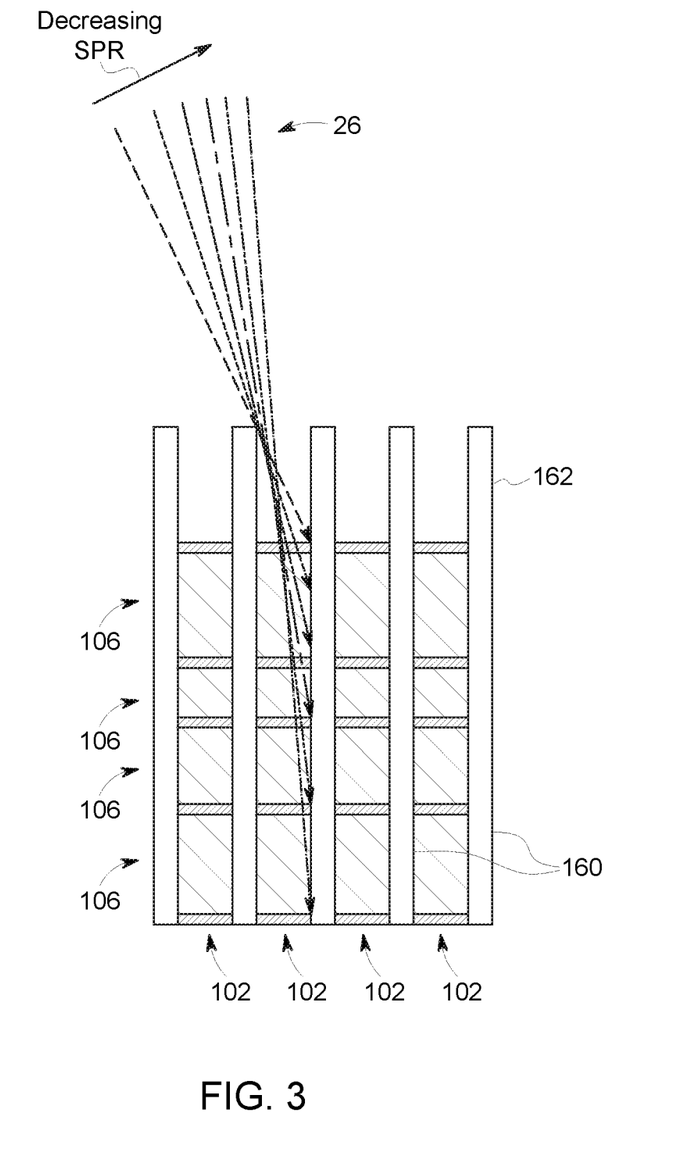
FIG. 3 depicts collimation effects of plates separating detector elements of the detector of FIG. 2, in accordance with aspects of the present disclosure.

With the context provided by FIGS. 1 and 2 in mind, the present approach leverages the observation that segments 106 closer to the surface of the detector element 102 facing the X-ray source 12 have a higher SPR ratio than those segments 106 lower in the detector element 102. This is shown visually in FIG. 3, where vertically segmented detector elements are shown in conjunction with X-rays 26 having a range of angles of approach. As may be seen, due to the collimating effects of the anti-scatter septa 162 and separating plates 160, higher segments 106 can have incident X-rays approach from a greater angular range (i.e., a greater acceptance angle) than lower segments. Thus, the SPR for the vertically arranged segments 106 in a pixel 102 can be estimated from the known geometry of the detector. With this in mind, the present approaches use the readout signals acquired from the segments 106 within a detector element 102 to estimate scatter throughout the detector element 102. In one such approach, the depths of the respective segments 106 within a detector element can be used as a parameter in the modeling of the scatter signal, where deeper segments have less scatter signal. In one implementation, the readout signals from the lowest (i.e., bottom) segment 106A, which has the least or no scatter contamination, may be assumed to be all primary signal, and this signal may be used to correct the readout signals of higher segments 106 (which have a proportionately greater scatter signal as depth decreases) within the respective detector element 102. However, in general, determining both the primary and scatter signals of each detector element 106 may be a joint estimation process using the readout information from some or all segments 106 within a given detector element 102. In accordance with these approaches, pixel-by-pixel scatter correction may be implemented that provides accurate estimation for the scatter signal for each readout layer.

Figure 4:
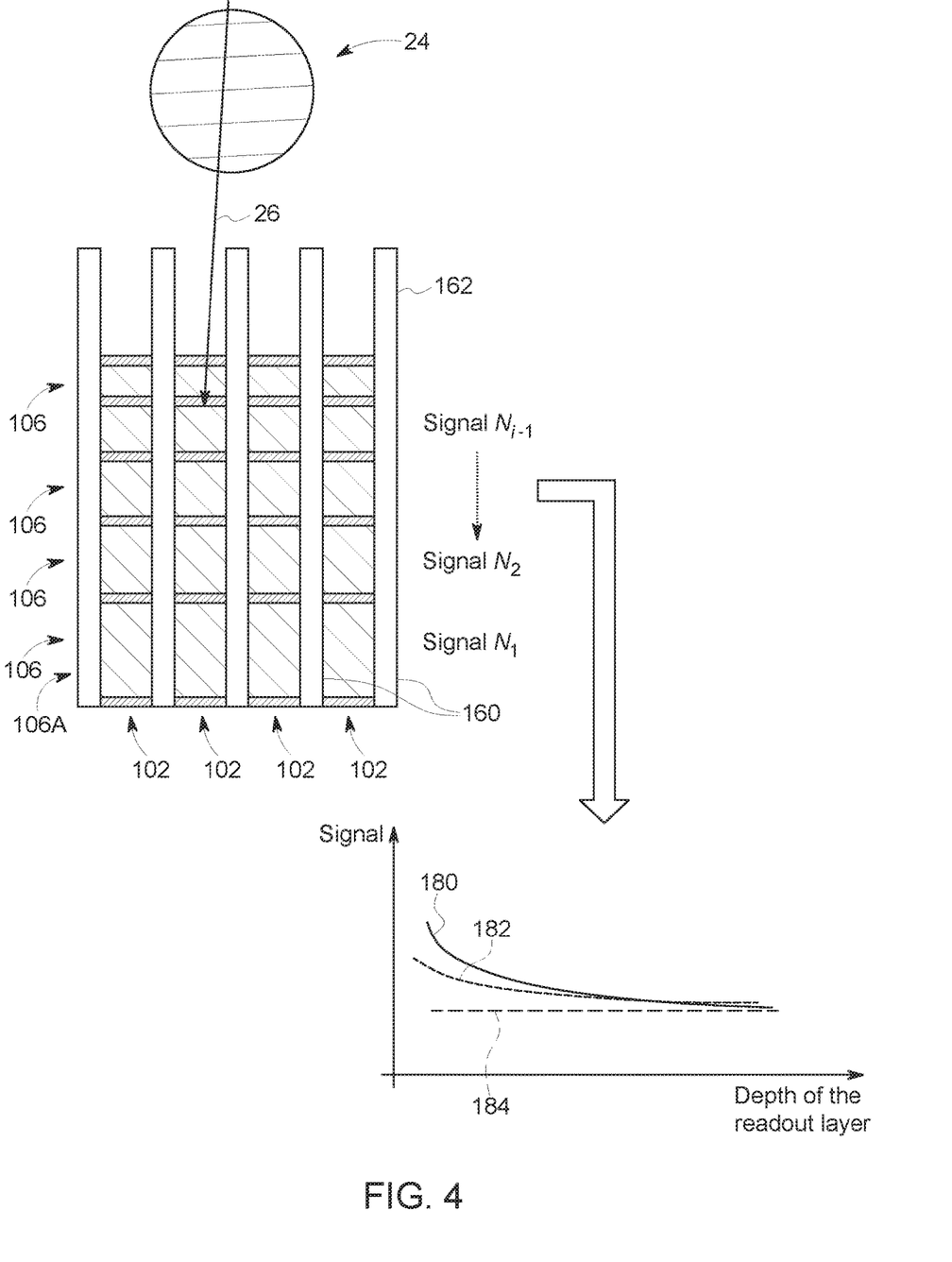
FIG. 4 depicts combined primary and scatter signals of a segmented detector, in accordance with aspects of the present disclosure.

By way of example, and turning to FIG. 4, in a first implementation the measured signal, $N_i$, for each readout layer i (i.e., the different depths at which segments 106 are formed in conjunction with the corresponding associated readout channel), is composed of primary signal $P_i$ and scatter signal $S_i$:

$$N_i = P_i + S_i \quad (1)$$

The segment thicknesses have been designed so that the primary signal is approximately constant for the different readout layers, though the scatter signal at each readout layer differs, with decreasing scatter signal the lower the readout layer. This is shown graphically in the graph of FIG. 4 where line 180 corresponds to measured signal $N_i$, line 182 corresponds to primary signal $P_i$, and line 184 corresponds to scatter signal $S_i$.

With this in mind, the scatter signal from the bottom layer (here layer 1) of the detector 28 (associated with bottommost segments 106A) is well shielded from the scattered X-ray photons. The scatter signal in the bottom layer, $S_1$, is approximately zero. So, the measured signal in the bottom layer can be estimated as:

$$P_1 = N_1 \quad (2)$$

Figure 5:
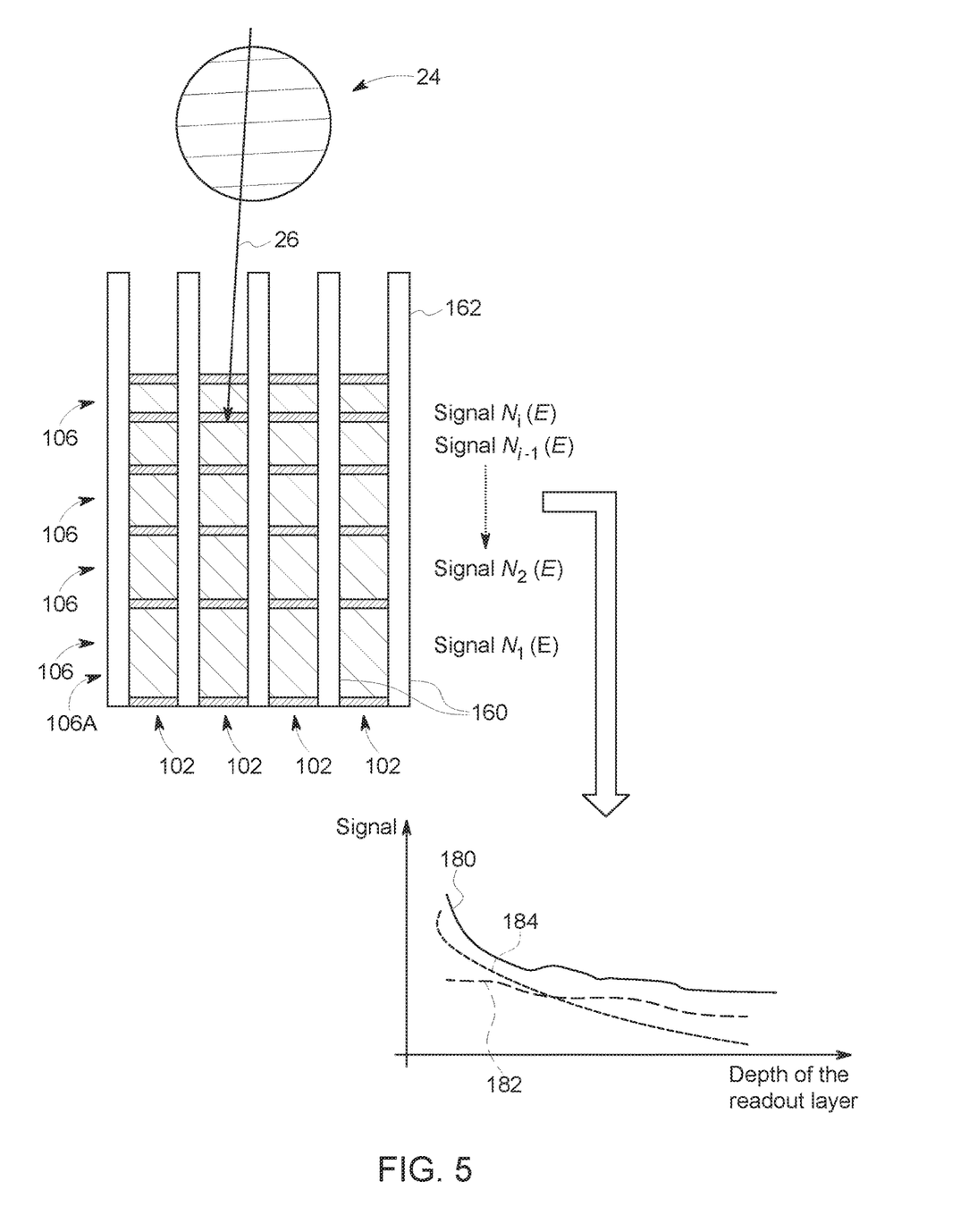
FIG. 5 depicts combined primary and scatter signals of a segmented detector, in accordance with aspects of the present disclosure.

With the preceding in mind, and turning to FIG. 5, an example algorithm taking into account spectral information is shown. For a Si-strip photon counting detector, as discussed herein, the spectrum of the primary signal $P(E)_i$ is resolved for each readout layer. Given this spectrum information, a scatter estimation can be performed for the upper readout layers using the signal from a lower readout layer, such as the bottom readout layer corresponding to bottommost segments 106A. The primary signal in the remaining (i.e., non-bottom) layers can be estimated by assuming the signal that reached the bottom (or other lower) readout layer was attenuated by the layers above it.

For example, let $\mu(E)$ be the X-ray attenuation coefficient of the silicon detector material for X-rays of energy E. If the X-ray photon flux reaching the detector surface is denoted as $I_i$, then by Beer's law, the X-ray photon flux after being attenuated by the top detector layer is:

$$I_{i-1} = I_i e^{-\mu(E) d_i} \quad (3)$$

where $d_i$ is the thickness of the corresponding detector layer. The X-ray photon flux after being attenuated by the second top detector layer is:

$$I_{i-2} = I_i e^{-\mu(E)(d_i + d_{i-1})} \quad (4)$$

Similarly, the X-ray photon flux after being attenuated by the bottom detector layer is:

$$I_0 = I_i e^{-\mu(E)(d_i + d_{i-1} + \ldots + d_1)} \quad (5)$$

And the X-ray photon flux after being attenuated by the second layer from the bottom is:

$$I_1 = I_i e^{-\mu(E)(d_i + d_{i-1} + \ldots + d_2)} \quad (6)$$

Therefore, the primary signal P for each detector layer can be calculated. The primary signal for the bottom detector layer is:

$$P_1 = I_2 - I_1 = I_i e^{-\mu(E)(d_i + \ldots + d_3)}(1 - e^{-\mu(E) d_2}) \quad (7)$$

The primary signal for the second layer from the bottom detector layer is:

$$P_2 = I_2 - I_1 = I_i e^{-\mu(E)(d_i + \ldots + d_3)}(1 - e^{-\mu(E) d_2}) \quad (8)$$

The primary signal for the top layer is:

$$P_i = I_i(1 - e^{-\mu(E) d_i}) \quad (9)$$

The primary signal for the second layer from the top detector layer is:

$$p_{i-1} = I_i e^{-\mu(E) d_i}(1 - e^{-\mu(E) d_{i-1}}) \quad (10)$$

The ratio for the signals for each detector layer compared to the bottom detector layer can be calculated with these equations. For example:

$$\frac{P_2}{P_1} = \frac{e^{\mu(E) d_2}(1 - e^{-\mu(E) d_2})}{1 - e^{-\mu(E) d_1}} \quad (11)$$

$$\frac{P_i}{P_1} = \frac{e^{\mu(E)(d_i + \ldots + d_2)}(1 - e^{-\mu(E) d_i})}{1 - e^{-\mu(E) d_1}} \quad (12)$$

A least square fitting can be performed giving the measured signal N together with the relationship between the primary signals to estimate the primary signal P and scatter signal S for each readout layer of the detector 28. Since the scatter signal is a low frequency signal, a smoothing kernel can also be applied to further smooth the scatter signal from the fitting operation. In an implementation with 30 mm height of the tungsten layer, the scatter signal $S_1$ for the bottom layer can be ignored, therefore, the signal for the bottom layer can be treated as primary signal only, to simplify the least square fitting.

Figure 6:
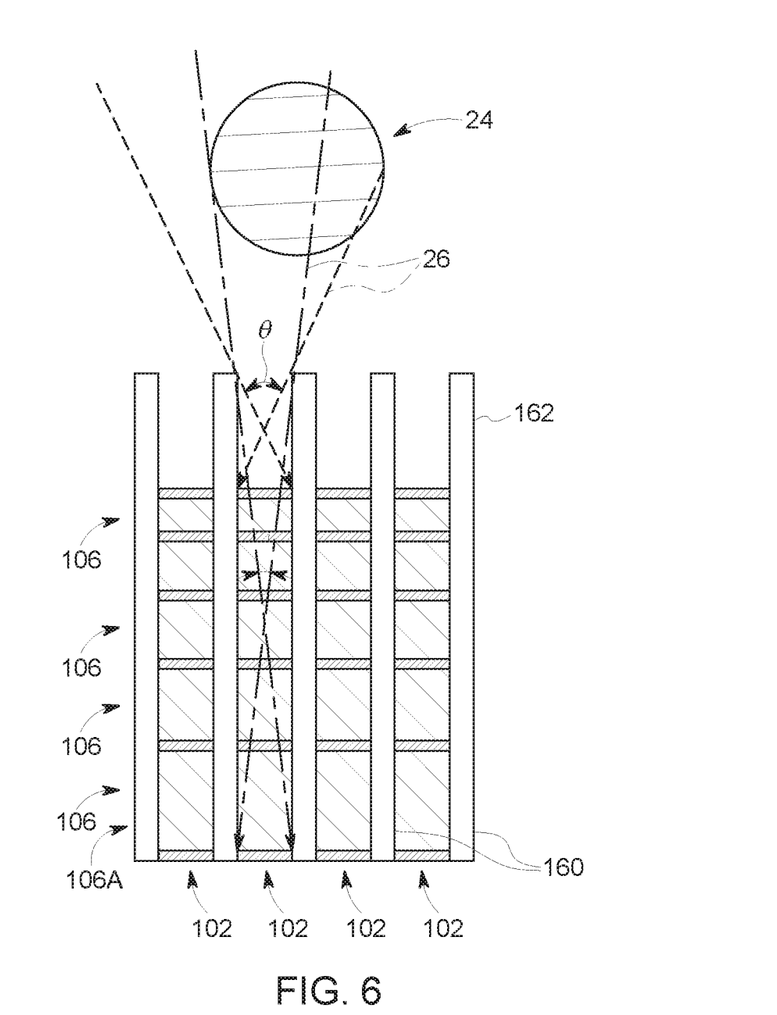
FIG. 6 depicts geometrics aspects of scatter with respect to a segmented detector, in accordance with aspects of the present disclosure.

In a second implementation, the scatter signal $S_i$ for each detector readout layer has a dependence on the signal collection angle (i.e., accepting or acceptance angle) θ for each detector readout layer, as shown in FIG. 6, and a model based scatter correction algorithm is derived from this dependence. Given the design geometry, the acceptance angle $\theta_i$ for each detector layer can be calculated. The scatter signal $S_i$ at a given readout layer, which decreases from the top readout layer to the bottom readout layer, is a function of $\theta_i$ and can be modeled as $(\theta_i)$. The acceptance angle $\theta_i$ depends on the depth d of the detector readout layer, which can be characterized as $\propto \tan^{-1} w/d$, where w is the width of the detector pixel 102.

To accurately model the scatter signal, the size of the object 24 and the size or dimensions of the pre-patient collimator 22 also needs to be taken into account. For example, if the object 24 is too small, the detector cells far away from the object may receive much less scatter signal. If the pre-patient collimator 22 is very narrow, the amount of scatter signal from the object is also much less.

By way of example, if the object 24 is big enough to cover the majority of the detector plane, and the pre-patient collimator 22 is wide, the scatter signal arriving at the top detector readout layer is referred to as $S_c$. As the acceptance angle decreases, the scatter signal S will generally decrease proportionally:

$$S \propto \theta \propto \tan^{-1} \frac{w}{d} \quad (13)$$

Therefore, for the top detector layer i:

$$N_i = P_i + S_c \tan^{-1} \frac{w}{d_i} \quad (14)$$

For the second detector layer from the top, i−1:

$$N_{i-1} = P_{i-1} + S_c \tan^{-1} \frac{w}{d_i + d_{i-1}} \quad (15)$$

Similarly, for the bottom detector layer:

$$N_1 = P_1 + S_c \tan^{-1} \frac{w}{d_i + \ldots + d_1} \quad (16)$$

This scatter signal relationship can also be used in a least square fitting scheme as described above since the measurement signal for each detector readout layer is available to solve for the primary signal P and the scatter signal S. The amount of scatter signal $S_c$ from the object 24 can also be obtained using a physics model-based scatter estimation. In addition, a first-pass reconstruction can also be applied to better estimate the scatter signal S. This dependence can also be used to model the scatter signal for each readout layer, and combined with the previously described algorithm to further improve the estimation accuracy of the scatter signal.

Figure 7:
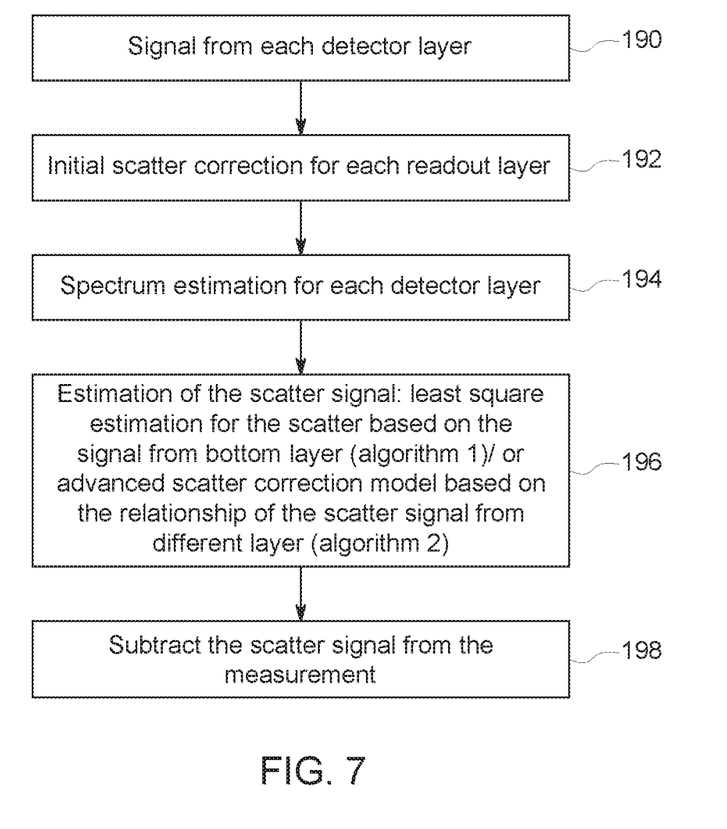
FIG. 7 is a flow chart of a method for scatter-correction, in accordance with aspects of the present disclosure

Turning to FIG. 7, an example process flow describing steps for performing a scatter correction process for an energy-resolving detector having multiple readout layers is shown. In this example flow, at step 190 a readout signal is acquired from each readout layer (corresponding to the different depths of the segments 106 of a multi-segment detector element 102). An initial scatter correction for each readout layer is performed at step 192. This step is also optional. Spectrum information is estimated (step 194) for each readout layer. Based on the initial scatter correction and spectrum estimation, the scatter signal is estimated (step 196) for each readout layer, such as using a least square estimation based on the signal from the bottom readout layer for a given pixel 102. Alternatively, a scatter correction model may be employed that is based on the relationship of the scatter signal between different readout layers of a given pixel. The estimated scatter signal is then subtracted (step 198) from the measured signal for a given segment 106 of the respective pixel 102.

Figure 8:
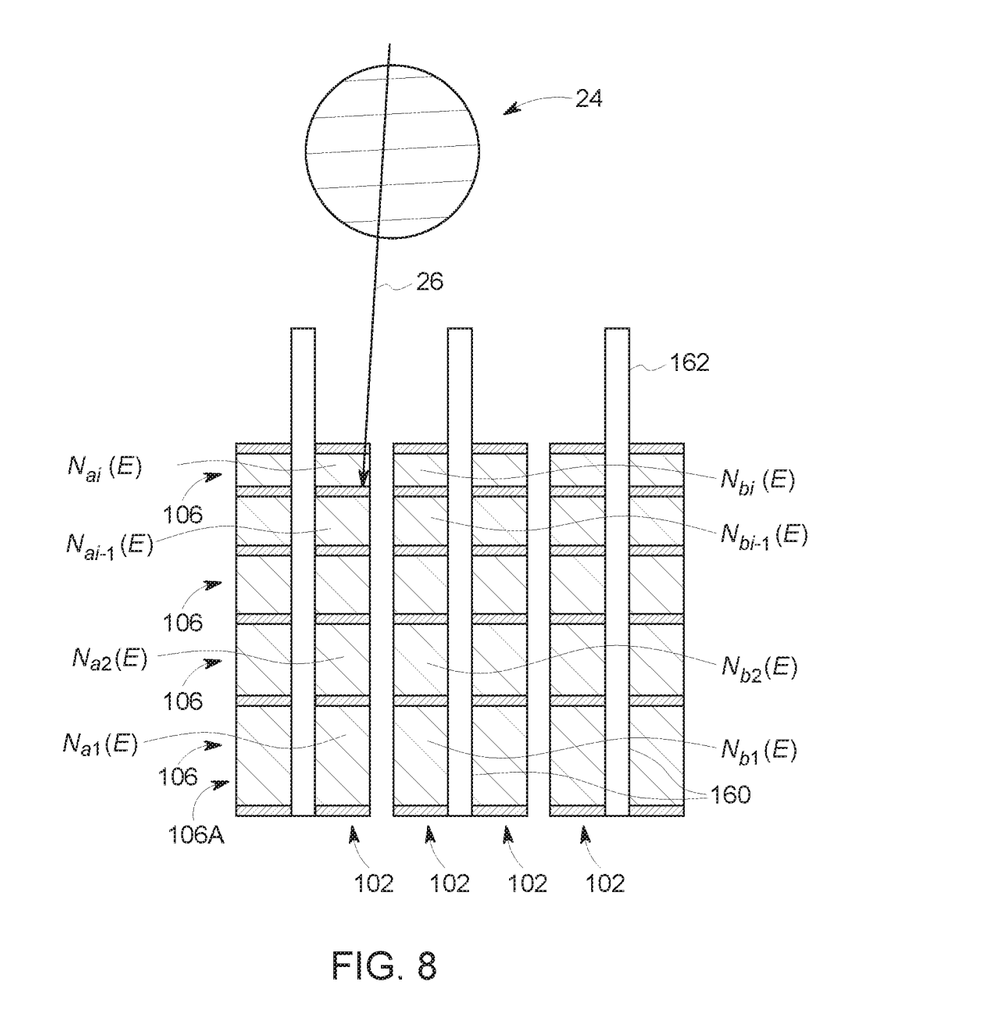
FIG. 8 depicts aspects of scatter with respect to a segmented detector with alternating collimation, in accordance with aspects of the present disclosure.

It may be appreciated that, while the preceding examples provide a general overview of the present concepts, the present approach is also applicable with variations of the above-described detector configurations. For example, the scatter collimator plates or reflectors 160 do not have to be disposed between each row of pixels 102, but may instead be positioned between alternating rows of pixels 102 or in accordance with other alternation schemes (i.e., every second, every third, or every forth row of pixels), as shown in FIG. 8. The proposed algorithm is equally applicable to these designs.

By way of example, and turning to FIG. 8, scatter signals typically have low special frequency, i.e., adjacent pixels receive similar scatter signals. Therefore, the readout values of pixels between a set of plates 160 can be averaged for scatter signal estimation to improve the statistics in accordance with:

$$N_i(E) = (N_{ai}(E) + N_{bi}(E))/2. \tag{17}$$

Scatter estimation can then be performed on the averaged signals using the previously described algorithm for signal sequence $N_i(E)$.

Figure 9:
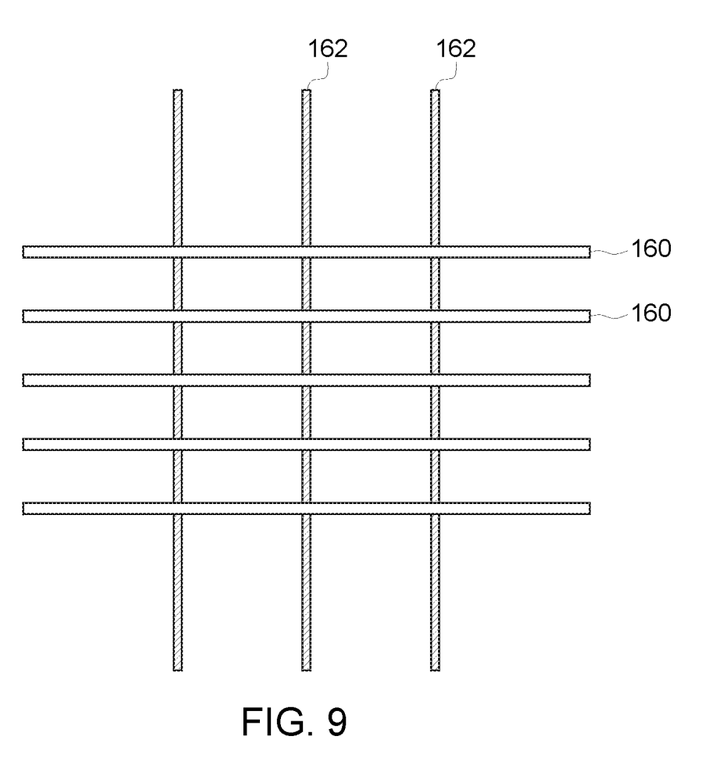
FIG. 9 depicts a two-dimensional collimation grid, in accordance with aspects of the present disclosure.

In one implementation, as discussed herein, a deep 1-D anti-scatter collimator along the X-direction (plates 160) can reduce the scatter signal significantly. In addition, another anti-scatter collimator along the Z-direction (plates 162) can further reduce the scatter signal, as shown in a top-down view in FIG. 9. In particular, the readout signal from the bottom readout layer, corresponding to segments 106A, may be treated as the primary signal in this instance. As may be appreciated, the primary signal should be approximately constant, taking into account the spectrum of the primary signal, between segments 106 of a properly aligned pixel 102, and may thereby be determined for the other readout layers of a pixel 102 given the spectrum information, as discussed in certain of the preceding examples.

Various systems and methods for estimating and/or reducing scatter signal in a radiation detector, such as on a pixel-by-pixel basis, are described herein. Such individual pixel based scatter correction algorithms can significantly improve the accuracy of scatter signal estimation for CT or other imaging systems. With the improved scatter correction, the image quality may be expected to improve accordingly by reducing artifacts, which may have benefits in diagnosing disease. Further, the present approach leverages the detector design itself of a photon-counting detector based on silicon strip and may simplify detector design by reducing or eliminating the anti-scatter collimator.

It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

While the technology has been described in detail in connection with only a limited number of embodiments, it should be readily understood that the specification is not limited to such disclosed embodiments. Rather, the technology can be modified to incorporate any number of variations, alterations, substitutions or equivalent arrangements not heretofore described, but which are commensurate with the spirit and scope of the claims. Additionally, while various embodiments of the technology have been described, it is to be understood that aspects of the specification may include only some of the described embodiments. Accordingly, the specification is not to be seen as limited by the foregoing description, but is only limited by the scope of the appended claims.

The invention claimed is:

1. A method for reducing scatter signal in a computed tomography (CT) system comprising an X-ray source and a pixelated detector, the method comprising:
    for each respective segment of a detector element comprising a plurality of segments disposed at a plurality of depths with respect to the surface of the detector element facing the X-ray source, acquiring a respective response signal;
    for the detector element, estimating a scatter signal at one or more segments of the detector element based on an acceptance angle of the respective segment of the detector element, wherein the acceptance angle depends on the depth of the respective segment of the detector element; and
    based upon the estimated scatter signal, estimating a primary signal substantially free of scatter at one or more segments of the plurality of segments to generate scatter-corrected readout signals.

2. The method of claim 1, wherein the primary signal is estimated based upon a respective readout signal from a respective segment furthest from the X-ray source.

3. The method of claim 1, wherein the primary signal and the scatter signal are jointly estimated using the readout signals from all segments of the detector element, with readout signals from segments further from the X-ray source receiving greater weighting in the joint estimation process.

4. The method of claim 1, wherein the act of estimating the scatter signal is based upon one or both of dimensions of an imaged object or the geometry of the X-ray source and detector.

5. The method of claim 1, wherein the act of estimating the scatter signal is based upon a respective X-ray spectrum estimated for each segment of the detector element.

6. The method of claim 1, wherein the act of estimating comprises applying a least square fitting operation.

7. The method of claim 1, wherein the act of estimating employs a physics-based scatter model to estimate the scatter signal at the other segments of the detector element.

8. The method of claim 7, wherein the physics based scatter model includes a parameter for the receiving angle for each of the segments of the detector element.

9. The method of claim 1, further comprising smoothing the estimated scatter signal.

10. The method of claim 1, wherein the act of estimating is performed on averaged measured signals from corresponding segments of adjacent detector elements.

11. The method of claim 1, wherein the acceptance angle (θ) of the respective segment of the detector element is characterized as [θ α tan$^{-1}$(w/d)], where w is the width of the detector element and d is the depth of the respective segment.

12. The method of claim 1, wherein the ratio of the primary signal of a segment of the detector element ($P_i$) with respect to the primary signal of the bottommost segment ($P_1$) of the detector element is given as:

$$\frac{P_i}{P_1} = \frac{e^{\mu(E)(d_i+\ldots+d_2)}(1 - e^{-\mu(E)d_i})}{1 - e^{-\mu(E)d_2}}$$

where i is a number of the segment of the detector element with respect to the bottommost segment, d is the depth of the respective segment and μ(E) is an X-ray attenuation coefficient of the detector element material for X-rays of energy E.

13. A computed tomography (CT) imaging system, comprising:
an X-ray radiation source configured to emit X-ray radiation;
a pixelated detector configured to generate X-ray signals in response to the emitted X-ray radiation, wherein the pixelated detector comprises a plurality of detector elements, each detector element comprising a plurality of segments offset in the direction of X-ray radiation propagation at a plurality of depths, wherein at least a portion of the detector elements are separated by X-ray radiation blocking plates in at least one dimension;
a processing component configured to receive X-ray signals read out from the pixelated detector, wherein an X-ray signal is read out for each segment of each detector element, and wherein for each detector element the processing component:
estimates a scatter signal at one or more segments of the detector element based on an acceptance angle of the respective segment of the detector element, wherein the acceptance angle depends on the depth of the respective segment of the detector element
based upon the estimated scatter signal, estimates a primary signal substantially free of scatter at one or more segments of the plurality of segments to generate scatter-corrected readout signals; and
for the combined scatter corrected readout signals from each detector element, reconstructs an image using the scatter corrected readout signals.

14. The CT imaging system of claim 13, wherein the primary signal and the scatter signal are jointly estimated using the readout signals from all segments of the detector element.

15. The CT imaging system of claim 14, where the readout signals from segments further from the X-ray radiation source have less scatter signal which can be modeled using the depth of the segment as one parameter.

16. The CT imaging system of claim 13, wherein the primary signal is estimated based upon a respective readout signal from a respective segment furthest from the X-ray radiation source.

17. The CT imaging system of claim 13, wherein the detector elements are separated by X-ray radiation blocking plates in intervals of every pixel, every second pixel, every third pixel, every fourth pixel, or every fifth pixel.

18. The CT imaging system of claim 13, wherein the processing component is further configured to estimate the scatter signal based upon one or both of dimensions of an imaged object or the geometry of the X-ray source and detector.

19. The CT imaging system of claim 13, wherein the processing component is further configured to estimate the scatter signal based upon a respective X-ray spectrum estimated for each segment of the detector element.

20. The CT imaging system of claim 13, wherein the processing component is further configured to estimate the scatter signal using averaged measured X-ray signals from corresponding segments of adjacent detector elements.

* * * * *